United States Patent [19]

Kawada et al.

[11] Patent Number: 5,270,045
[45] Date of Patent: Dec. 14, 1993

[54] METHOD OF USING A BAIT COMPOSITION FOR CONTROLLING VERMIN

[75] Inventors: Hiroshi Kawada; Haruki Kanasugi; Kenichi Tanaka; Izumi Yamane, all of Tokyo, Japan

[73] Assignee: Hodogaya Chemical Co., Ltd., Tokyo, Japan

[21] Appl. No.: 867,292

[22] Filed: Apr. 10, 1992

Related U.S. Application Data

[63] Continuation of Ser. No. 526,178, May 21, 1990, abandoned.

[30] Foreign Application Priority Data

May 30, 1989 [JP] Japan .................................. 1-134600

[51] Int. Cl.$^5$ ..................... A01N 25/08; A01N 25/12; A01N 25/34

[52] U.S. Cl. .................................. 424/410; 424/405; 424/408; 424/409

[58] Field of Search ................ 424/410, 405, 408, 409

[56] References Cited

U.S. PATENT DOCUMENTS 4,826,682  5/1989  Sakharova ........................ 424/623

FOREIGN PATENT DOCUMENTS 62-19502   1/1987  Japan .
5629924    6/1992  Japan .
743958    11/1952  United Kingdom .
2030045    9/1979  United Kingdom .

Primary Examiner—Thurman K. Page
Assistant Examiner—C. Azpuru
Attorney, Agent, or Firm—Paul & Paul

[57] ABSTRACT

A bait composition comprising 3,5-xylyl N-methylcarbamate contained in a bait material, and useful for exterminating vermin by lure feeding.

3 Claims, No Drawings

METHOD OF USING A BAIT COMPOSITION FOR CONTROLLING VERMIN

This is a division of application Ser. No. 07/526,178, filed May 21, 1990 which is now abandoned.

BACKGROUND OF THE INVENTION

1) Field of the Invention

The present invention relates to a method of using a bait composition for controlling vermin. More particularly, the present invention relates to a method of using a bait composition useful for exterminating agriculturally noxious terrestrial mollusca which are difficult to control, for example, slugs (incilaria) and snails; noxious aquatic mollusca, for example, pond snails; harmful and unpleasant insects and arthropods (isopoda) which often destroy crops, for example, pillbugs and sowbugs, ants and crickets.

2) Description of the Related Arts

It is known that a molluscs-killing agent containing, as an effective component, metaldehyde (metaacetoaldehyde) is widely utilized to exterminate agriculturally noxious terrestrial mollusca, for example, slugs and euhadra-helix. Nevertheless, there are very few expellent agents which do not harm humans and are effective for exterminating pond snails, which are noxious to paddy-rice plants, and currently only lime nitrogen is utilized for this purpose.

Further, in general, to exterminate unpleasant vermin, for example, sowbugs and ants, 1-naphthyl N-methylcarbamate (hereinafter referred as "NAC") mixed with metaldehyde, which is usually used to exterminate terrestrial mollusca, is employed for home use.

Conventional lure-killing agents for vermin, consisting of a killing agent for mollusca, mixed with a luring bait material, do not always have a satisfactory vermin-killing activity and spectrum, and therefore, the conventional lure-killing agents must contain a high concentration of the effective component, or require two or more effective components to enhance the activity and spectrum thereof, and therefore, are not widely employed to protect edible plants.

SUMMARY OF THE INVENTION

An object of the present invention is to provide a method of using a bait composition for controlling vermin, which composition is safe and has a high control activity and a wide control spectrum for a variety of vermin, even when containing a low concentration of an effective component.

The above-mentioned object can be attained by the bait composition of the present invention for controlling vermin, which composition comprises 3,5-xylyl N-methylcarbamate contained in a bait material.

DESCRIPTION OF THE PREFERRED EMBODIMENTS

The inventors of the present invention carried out intensive research into the providing of controlling agents for vermin, such as terrestrial mollusca, and as a result, discovered for the first time that, when fed, 3,5-xylyl N-methylcarbamate (hereinafter referred to as "XMC") has an excellent exterminating activity not only for the noxious terrestrial mollusca, but also for harmful aquatic mollusca, insects, and arthropods (homopoda). Note, it is important that the XMC be utilized by feeding the vermin through the mouth but not the respiratory organ thereof, to exterminate same.

XMC has the formula (I):

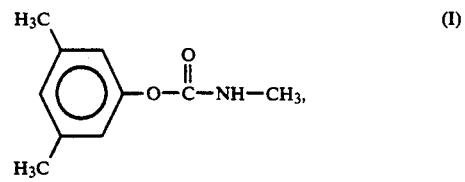

usually in the form of a white powder, and is soluble in most organic solvents.

In the vermin-controlling bait composition of the present invention, the XMC is preferably contained in an amount of 0.5% to 5% by weight, more preferably 1% to 3% by weight, in a bait material, to ensure the vermin-controlling effect thereof.

The bait material usable for the present invention is not limited to specific types of edible materials, and usually comprises at least one member selected from the group consisting of soybean oil draff, wheat flour, rice bran, biscuit powder and potato, which are edible materials for luring vermin.

The vermin-controlling bait composition of the present invention can be prepared in such a manner that a predetermined amount of the XMC is mixed with the vermin-luring edible material, the mixture is pulverized and kneaded together with water, the resultant paste is pelletized in predetermined shapes and dimensions, and the paste pellets are dried to provide dry pellets.

The shape and dimensions of the pellets are variable depending on the use thereof but usually the pellets are in the form of a short rod having a length of 1 to 10 mm and a diameter of 1 to 5 mm.

In another process for preparing the vermin-controlling bait composition of the present invention, a bait material, for example, dried potato chips, are impregnated with a solution of the XMC in a solvent, for example, ethylalcohol and their dried.

The vermin-controlling bait composition of the present invention can be applied in a usual manner for controlling vermin, for example, by placing in an area in which the plants to be protected are cultivated or on a plant cultivating shelf.

EXAMPLE

The present invention will be further explained by way of specific examples, which are merely representative and do not in any way restrict the scope of the present invention.

EXAMPLES 1 AND 2 AND COMPARATIVE EXAMPLES 1 TO 5

In each of Examples 1 and 2, bait composition pellets were prepared by mixing the XMC in the amount as indicated in Table 1 with a luring bait material obtained by mixing 70% by weight of soybean oil draff with 30% by weight of wheat flour, and by pulverizing the bait mixture; kneading the resultant mixture together with water, pelletizing the resultant paste to form a number of short-rod-shaped pellets having a diameter of 2 mm and a length of 3 to 7 mm, and drying the pellets.

The bait composition pellets in an amount of 3 g were placed on a plastic resin plate having a diameter of 9 cm, and left to stand below a plant cultivating shelf in a greenhouse for three days, to lure-kill slugs, and thereafter, the number of lure-killed slugs were counted.

In each of Comparative Examples 1 and 2, the same procedures as mentioned above were carried out, except that the XMC was replaced by NAC in the amount as indicated in Table 1.

In each of Comparative Examples 3 and 4, the same procedures as in Examples 1 and 2 were carried out, except that the XMC was replaced by metaldehyde in the amount as shown in Table 1.

In comparative Example 5, the same procedures as in Example 1 were carried out, except that the vermin-controlling component was omitted from the bait composition.

In such of the examples and comparative examples, the feeding test was repeated 25 times. The results are shown in Table 1. Note, the results are statistically treated in accordance with Duncan's new multiple range test method, to determine significant differences between the average values of the results of the lure-killing tests in each of the example and comparative examples. The result of the statistical examination is also shown in Table 1.

TABLE 1

| Example No. | Vermin-controlling component Type | Amount (% by wt.) | Number of lure-killed vermin ± standard deviation per feeding plate | Indication of significant differences using Duncan's test method (*) | | | |
|---|---|---|---|---|---|---|---|
| Example 1 | XMC | 1 | 5.4 ± 6.0 | a | b | | |
| 2 | " | 3 | 7.0 ± 8.6 | a | | | |
| Comparative 1 | NAC | 1 | 1.5 ± 2.1 | | | c | d |
| ative 2 | " | 3 | 3.3 ± 3.5 | | b | c | |
| Example 3 | Metaldehyde | 1 | 4.0 ± 4.4 | a | b | c | |
| 4 | " | 3 | 4.4 ± 6.0 | a | b | c | |
| 5 | None | — | 00 ± 00 | | | | d |

Note: (*)Each of the lower case alphabetical characters indicates that no significant difference can be found between average values indicated by the same lower-case alphabetical characters in a level of significance of 5% in accordance with Duncan's new multiple range test method.

Table 1 shows that the vermin-controlling bait compositions of Examples 1 and 2 have a higher efficiency for lure-killing slugs than those of Comparison Examples 1 to 5.

EXAMPLES 3 AND COMPARATIVE EXAMPLE 6

In Example 3, thin potato chips were dried under vacuum and immersed in a solution of 1% by weight of XMC in ethyl alcohol, at room temperature for 6 hours, and the resultant XMC-impregnated potato chips then dried in the ambient atmosphere at room temperature. The resultant dried potato chips contained 1.7% by weight of XMC. In a plastic pot having an inside bottom area of 1/5000 are, were placed one liter of water, 10 pond snails, and 3 g of the XMC-impregnated potato chips, and after three days, the number of dead or living pond snails were counted.

In Comparative Example 6, the same procedures as in Example 3 were carried out except that the dried potato chips were not impregnated with XMC.

The results are shown in Table 2.

TABLE 2

| Example No. | Amount of XMC (% by wt.) | Number of pond snails | |
|---|---|---|---|
| | | Living | Dead |
| Example 3 | 1.7 | 0 | 10 |
| Comparative Example 6 | 0 | 10 | 0 |

EXAMPLE 4

A bait material was prepared by mixing 25% by weight of biscuit powder, 25% by weight of soybean oil draff, 25% by weight of parched rice bran, and 25% by weight of wheat flour, and pulverizing the mixture.

Then a bait composition was prepared by mixing 97% by weight of the bait material with 3% by weight of XMC powder. The resultant bait composition was kneaded together with water in an amount of 30% based on the total weight of the bait material, the resultant paste was pelletized to form pellets having a diameter of 2 mm and a length of from 3 to 7 mm, and the resultant pellets were dried.

An amount of 3 g of the bait composition pellets was placed in on each of a plurality of plastic resin plates having a diameter of 9 cm.

The plates containing the pellets were left to stand in a plurality of places in a garden, for 3 days, and thereafter, the numbers of lure-killed terrestrial mollusca, insects and homopoda on the plates were counted.

The above-mentioned procedures were repeated five times. The total number of lure-killed vermin per plate, and the standard deviation of the results of the test, are shown in Table 3.

TABLE 3

| Sort of vermin | Number of lure-killed vermin ± standard deviation |
|---|---|
| Slugs | 11.6 ± 5.6 |
| Snails | 0.8 ± 0.8 |
| Ants | 28.4 ± 22.7 |
| Earwigs | 1.6 ± 1.1 |
| Crickets | 0.6 ± 0.9 |
| Pillbugs | 1.2 ± 1.1 |
| Sowlugs | 4.4 ± 2.4 |

Tables 1 to 3 clearly indicate that the bait composition of the present invention comprising XMC as an effective component, and a bait material comprising, for example, food waste, is useful for lure-killing various vermin, for example, noxious mollusca, insects, and arthropods by lure-feeding, at a high extermination activity and wide spectrum for a variety of vermin, and therefore, is an industrially applicable material.

We claim:

1. A method of controlling noxious terrestrial and aquatic mollusca, by baiting a bait composition consisting essentially of an toxic amount of 3, 5-xylyl-N-methylcarbamate and a solid bait material wherein said bait material effectively kills said mollusca upon consumption.

2. The method as claimed in claim 1, wherein the 3, 5-xylyl-N-methylcarbamate is contained in an amount of 0.5 to 5% by weight.

3. The method as claimed in claim 1, wherein the solid bait material comprises at least one member selected from the group consisting of soybean oil draff, wheat flour, rice bran, biscuit powder and potato.